United States Patent [19]

Pastormerlo

[11] 4,269,997
[45] May 26, 1981

[54] TREATMENT OF UREA SOLUTIONS

[75] Inventor: Primo Pastormerlo, Mortara, Italy

[73] Assignee: Stamicarbon B.V., Netherlands

[21] Appl. No.: 56,551

[22] Filed: Jul. 11, 1979

[30] Foreign Application Priority Data

Jul. 24, 1978 [IT] Italy ................. 26020 A/78

[51] Int. Cl.³ ........................................... C07C 126/02
[52] U.S. Cl. ........................................ 564/73; 564/67
[58] Field of Search ........................ 260/555 A, 555 R

[56] References Cited

U.S. PATENT DOCUMENTS

| 3,356,723 | 12/1967 | Kaasenbrood | 260/555 A |
| 3,514,484 | 5/1970 | Wentworth | 260/555 A |
| 3,936,500 | 2/1976 | Kaasenbrood et al. | 260/555 A |
| 3,984,469 | 10/1976 | Guadalupi | 260/555 A |
| 4,036,878 | 7/1977 | Kaasenbrood | 260/555 A |
| 4,208,347 | 6/1980 | Pagani | 260/555 A |

Primary Examiner—Brian E. Hearn
Attorney, Agent, or Firm—Holman & Stern

[57] ABSTRACT

A process and a device for treating urea solutions coming from synthesis reactors and containing in addition to the formed urea also free ammonia, water and unreacted ammonium carbammate having two steps wherein in the first step, a substantial amount of ammonia is distilled while ammonium carbammate is only partially decomposed, and in the second step, the bulk of carbammate is decomposed and the residual ammonia is distilled.

4 Claims, 7 Drawing Figures

TREATMENT OF UREA SOLUTIONS

BACKGROUND OF THE INVENTION

The present invention relates to the treatment of urea solutions which come from synthesis reactors where ammonia ($NH_3$) and carbon dioxide ($CO_2$) are reacted under pressure and at high temperature to form urea, and which contain, in addition to the formed urea, free ammonia, unreacted ammonium carbammate and water together with other by-products, the treatment consisting of:
 (a) a first phase or step in which an important amount of $NH_3$ is distilled from the urea solution while decomposing only a reduced amount of carbammate; and
 (b) a second phase in which the major part of the undecomposed carbammate present in the so treated solution is decomposed preferably under the contemporaneous stripping action of fresh $CO_2$.

The invention concerns also a device for the embodiment of the above treatment.

In the industrial urea production by $NH_3$ and $CO_2$ synthesis, the so-called "stripping" technologies have been mostly used. According to such conventional technologies, the residual unreacted carbammate in the urea melt coming from the reactor, is decomposed at high pressure (decomposer or stripper operating at the reactor pressure), because of $NH_3$ or $CO_2$ which is present in large excess in the decomposer vapor phase. According to the German Auslegeschrift No. 1468628 (I) and Dutch patent application No. 7019056 (II) such excess is obtained by external supply at the stripper bottom of gaseous $NH_3$ (reference I) or $CO_2$ (Reference II), countercurrently with the urea melt.

According to U.S. Pat. No. 3,876,696 (III) the $NH_3$ excess is ensured by the fact that the urea solution feeding the stripper, is already rich in $NH_3$ and the carbammate decomposition takes place in an exchanger in which the liquid falls as a thin film.

Finally, according to the Italian Pat. No. 770,241 (IV) carbammate decomposition is achieved, at a pressure considerably lower than that of the synthesis reactor, in two stages in the second stage of which external ammonia is introduced countercurrently. With this system the residual $NH_3$ content in the treated urea melt is very high (35.7 wt.%) and expensive $NH_3$ recovery stages are required; pumping devices are also required to recycle to the reactor the carbammate solution available at lower pressure.

In the process and plants operating according to reference patents I, II, III, all vapors produced in the carbammate decomposition, together with the distilled free ammonia, and together with all $NH_3$ (reference I) or $CO_2$ (reference II) introduced at the decomposer bottom, flow upwards counter currently with the urea melt, which leaves the decomposer from the bottom.

This method causes high process flows (vapor and liquid flows) through the carbammate decomposer tubes. Sizing of decomposer tubes (tube number and diameter) becomes very critical and selection cannot be optimised in relation to the process performance, because of the limitations imposed by the necessity to avoid flooding phenomena. Such phenomena adversely affect the decomposer performance and might damage it, thus reducing its operating life. Furthermore, large quantities of passivating agent are generally needed to prevent corrosion of the large heated stainless steel surfaces of the above-mentioned falling-film decomposers. Air is generally injected into the decomposers, thus utilizing the passivating action of oxygen. However, the introduction of large amounts of air into the system is detrimental to conversion in the reactor. Inert materials also cause ammonia and $CO_2$ losses through urea plant units, while oxygen is a potential source of explosions.

OBJECTS AND SUMMARY OF THE INVENTION

An object of the present invention is a new treatment which does not show the above-mentioned draw-backs of the conventional systems.

Another object of the invention is a treatment process which can be put into effect by a particularly simple and efficient device.

The treatment process and related devices are conceived so as: to be free from sizing limitations and flooding phenomena and requiring small amounts of passivating agent; to be suitable for the treatment of urea melts produced in a reactor operating with high $NH_3/CO_2$ molar ratios and in consequence with high yields; to have long operating life; to produce urea melts with low carbammate residual content, using a small quantity of fresh stripping agent, if any.

Even if by preference the process is used according to the invention, with the two treatment steps at the same or lower pressure than the synthesis pressure, it is equally possible to operate the two stages at different pressures which also differ, if necessary, from the synthesis pressure.

This embodiment may be found suitable for those plants or processes where carbammate decomposition and synthesis are carried out at different pressures.

All the above-mentioned objects are achieved with the new process according to the invention which consists of: (a) a first phase or step in which mainly $NH_3$ is distilled from the urea solution and a reduced amount of ammonium carbammate is decomposed and (b) a second step in which in the so-treated solution the carbammate is decomposed and the residual $NH_3$ is distilled.

In an advantageous embodiment, the first step is carried out by heating the urea solution at a temperature of from 190° to 230° during a time period of less than 50 seconds, preferably from 3 to 12 seconds, the second step is carried out by heating the urea solution coming from the first treatment step at a temperature of from 190° C. to 230° C. for a time period of less than 60 seconds, preferably from 10 to 20 seconds.

According to a particular feature of the invention, the second step is carried out in the presence of a countercurrent of fresh $CO_2$. Such stripping agent can even be eliminated obtaining still better performances than with known art. In fact, the two decomposition zones with intermediate $NH_3+CO_2$ vapors separation zone still ensure a sufficient high $NH_3$ excess in second zone vapor phase where carbammate decomposition reaches very high yields without any stripping agent.

According to a particular embodiment of the invention the two phases of the treatment process can be performed in a new device (decomposer) formed by a central body with an upper head piece and a lower bottom piece, said central body including two zones: a first zone being formed by a heated tube bundle fed at the bottom by the urea melt coming from the synthesis reactor, such melt flowing upwards inside the tubes from the lower bottom piece to the upper head piece, concurrently with the vapors produced in this first zone by at least partial $NH_3$ distillation and reduced carbammate decomposition, caused by the tubes external heating; a second zone being also formed by a heated tube bundle fed at the top by the urea melt treated in the first zone and coming from the upper head piece, such melt flowing as thin liquid film downwards inside the tubes to the lower bottom piece, countercurrently with externally introduced $CO_2$ stripping agent from the bottom piece or countercurrently with the $NH_3$ rich vapors produced in this second zone only, if no stripping agent is used; the treated urea melt coming from the bottom of said second zone being collected in the lower bottom piece, while vapors coming from the top of both first and second zone, are collected in the upper head piece.

In a first embodiment of the invention the first and second zone tube sheets or walls are concentrical while in a second embodiment the tube plate sheets are located side by side.

BRIEF DESCRIPTION OF THE DRAWINGS

The different aspects and advantages of the invention will better appear from the description of the preferred embodiments represented in the attached drawing, where:

FIGS. 2 and 3 are two schematic frontal views of the relative apparatus; and

DETAILED DESCRIPTION OF THE INVENTION

Figure 1:
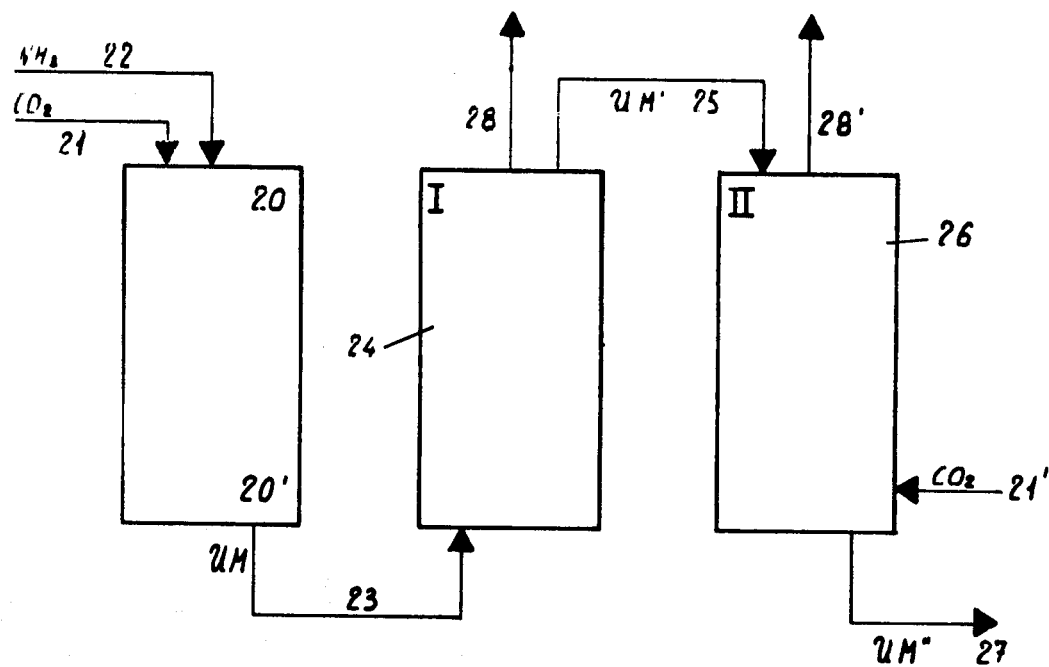
FIG. 1 is a schematic flow sheet illustrating the two-step treatment process of the invention.

The flow-sheet of FIG. 1 shows schematically the main feature of the treatment according to the invention. In a synthesis reactor 20, $NH_3$ fed through line 22 and $CO_2$ fed through line 21 are reacted under pressure and a high temperature and a urea melt UM (containing urea, ammonium carbammate, free $NH_3$ and other by-products) is obtained. Because generally the reactor 20 is fed through 22 with an excess of $NH_3$ over the stoichiometric ratio, the urea solution UM issuing in 20′ from the reactor 20 contains significant amounts of free $NH_3$ and of ammonium carbammate to be decomposed by thermal splitting into its single components, $NH_3$ and $CO_2$, which can then be recycled to the synthesis reactor 20. Conventionally this last is operated at high temperatures, (for example, 160°-250° C.) at a pressure of, for instance, 100-300 bars and with high $NH_3:CO_2$ ratios, for example, of from 2.5 to 10. The synthesis reaction is outside the scope of this invention which is concerned with the treatment of said urea melts UM. The treatment is schematically shown in the flow-sheet of FIG. 1 and consists in a thermal splitting carried out in two steps under critical conditions whereby:

(a) in step I a significant substantial amount of $NH_3$ is distilled from the urea solution UM, while decomposing only a small amount of carbammate. This step I is indicated with the diagram block 24 to which UM is fed from reactor 20 and from which the distilled vapors 28 are recovered and recycled to the reactor by conventional means.

(b) the so-treated urea solution UM′ is passed through line 25 to the second treatment step II shown as block 26, where the bulk of carbammate is now decomposed and the residual free $NH_3$ is distilled preferably by stripping UM′ in counter current with fresh $CO_2$ introduced in 21′; from step II are recovered through line 28′ and recycled to the reactor by conventional means the gases of the carbammate decomposition and the residual distilled $NH_3$, and through line 27 an urea solution UM″ having practically no free $NH_3$ and no carbammate is collected. The solution UM″ obtained from the process of the invention requires generally no further important treatment for $NH_3$ and $CO_2$ recovery.

The advantageous features of the treatment according to the invention will be better emphasized with the aid of the examples reported herebelow. It is, however, important to anticipate that in a particular application, the treatment can be carried out in very simple, efficient and cheap treating devices TD like the ones of FIGS. 2 and 3.

In the not limitative embodiment of said figures, a treating device TD is shown which consists of a central body CC (generally cylindrical with main size axial) included between a lower bottom piece F and an upper head piece T. The lower bottom piece F includes a liquid collector RL (urea melt free from carbammate and excess $NH_3$) and the let-down valve 5, while the upper head piece T includes a vapor collector RG with vapor let-down valve 4.

According to one embodiment of the invention, the central body CC is divided in two main zones, I Z and II Z (each zone being formed for example by a tube bundle containing a high number of long thin tubes). The central body CC, with the tube of Zones I Z and II Z, included within the side longitudinal walls Pl 1 and Pl 2, is separated from the lower bottom piece F by lower tube sheet Pi and from the upper head piece T by upper tube sheet Ps.

As it can be seen from the schematic section (FIG. 2b) of the embodiment shown in FIG. 2, the zone I Z is formed by an external tube bundle FTE of annular area shape inside of which the second zone II Z is located (internal tube bundle FTI). The tube bundle FTE of main zone I Z and FTI of main zone II Z lies between lower tube sheet Pi and upper tube sheet Ps. In the upper head piece T the baffle ST (with or without silts) located on the internal annular edge of tube sheet FTE, forms a liquid distribution path for the urea melt coming from the first zone I Z.

The urea melt UM coming from the urea reactor (not shown in FIGS. 2 and 3) is fed through a urea feed means shown as nozzles 3—3′ to the annular feed manifold CO (corresponding to line 23 in FIG. 1) located in the treating device bottom F and then flows upwards through tubes TU 1 of the first zone I Z to the upper head piece T where it is distributed by baffle ST into the tubes TU 2 of second zone tubes bundle FT I. The decomposer central body CC of the treating device TD is heated by first and second heat means (for example with steam) and in FIGS. 2 and 3, 1 and 2 are the heating medium inlet and outlet.

In the apparatus shown in FIGS. 2 and 3 as preferred embodiments of the invention, the treatment process according to the invention operates as follows:

(A) The urea melt containing ammonium carbammate, free ammonia, water, produced in the synthesis reactor (advantageously in a high yield reactor) is fed through nozzles 3—3′ to the annular feed manifold CO, located in the bottom F and connected with the first zone tube sheet FTE.

(B) Characteristically said solution flows upwards inside the tubes TU 1 of the first zone sheet FTE, being those tubes heated by steam introduced through connection 1. According to the main feature of the invention such heating and the flow speed (or residence time) of the urea solution are critically selected so that along tubes TU 1 only a small portion of carbammate is decomposed and an important portion of free ammonia is distilled from the urea melt UM: consequently said urea melt UM flows inside the tube 1 (up to the upper head piece T) concurrently with the vapors coming substantially from the $NH_3$ distillation and from the decomposition of carbammate. At this end, the temperature of tubes TU 1 is of from 190° to 220° C., the residence time of the urea solution UM is below 50 seconds and preferably from 3 to 12 seconds.

(C) In the upper head piece T at the first zone tubes TI 1 exit, separation takes place of vapors ($NH_3$, $CO_2$, $H_2O$) produced from the treated urea melt UM'; while said vapors are collected in the collector RG, the urea melt UM' builds up a level in the annular zone between the external wall Pl 1–Pl 2 and internal baffle ST and when the melt level reaches the ST upper edge it overflows into the central zone PC feeding the internal tube bundle FT 1 of zone II Z.

(D) Characteristically the urea melt UM' treated in I Z, feeds the tubes TU 2 of the second distillation zone II Z and, distributed as thin liquid-film inside such tubes TU 2, flows from top (upper head piece T) to bottom (lower bottom piece F) countercurrently with either fresh gaseous $CO_2$ flow introduced from outside in F through nozzles 6 (corresponding to line 21' in FIG. 1) or with the vapors produced in this second zone II Z only in the absence of any other fresh stripping agent. Because of the thin film distribution of the urea melt UM' inside tubes TU 2 and the second heat means (steam introduced through 1), a good contact between the urea melt UM' and the countercurrently moving fresh $CO_2$ flow or countercurrently moving vapors in the absence of fresh $CO_2$ is ensured and consequently a good stripping action takes place. Because of the good contact the distillation of carbammate and ammonia (still present in the urea melt UM' after the treatment in the first zone I Z) is completed in this second zone II Z.

According to a feature of the invention, the temperatures of the second zone tubes is from 190° C. to 230° C. while the residence time of UM' there is of from 10 to 20 seconds.

(E) The urea melt, which is introduced in the treating device TD through distributor CO of the bottom piece F after the first treatment achieved by upward transport through tubes TU 1 of the first zone I Z (concurrently with distilled vapors) and a second treatment achieved by downward transport through tube TU 2 of the second zone II Z as thin film countercurrently with vapor phase, is collected in the lower collector RL as urea solution UM" of high purity so as not to require further important treatment.

Figure 2A:
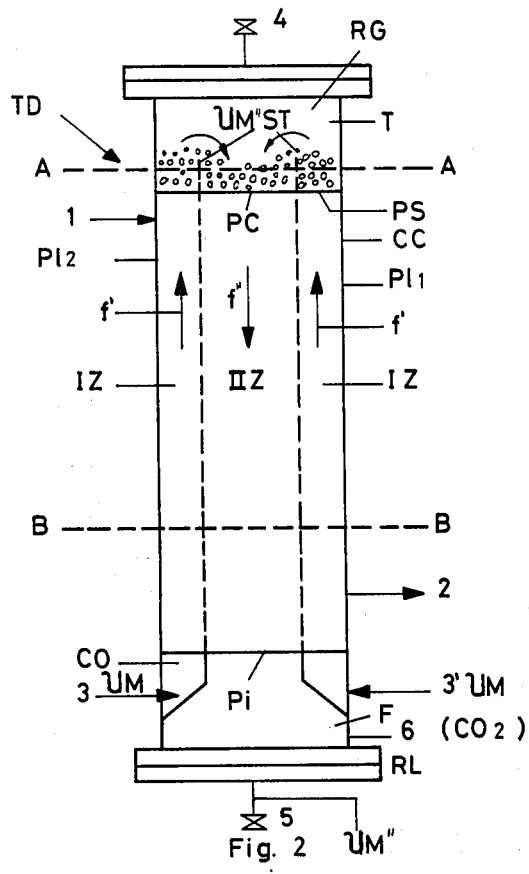
FIGS. 2a, 2b and 3a, 3b are schematic partial horizontal cross sections along lines A—A and B—B in FIGS. 2 and 3, respectively.
Figure 2A:
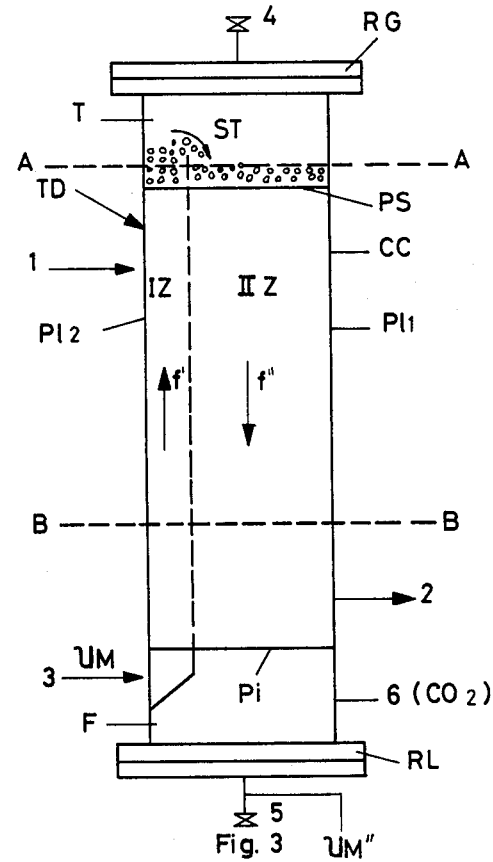
Figure 2A:
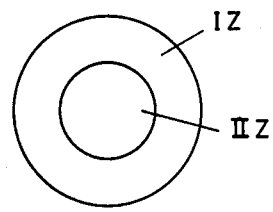
Figure 2B:
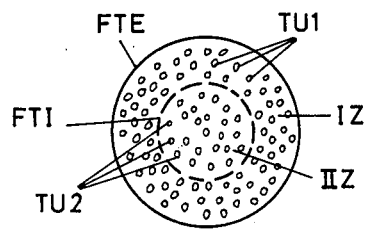

In FIGS. 2, 2a and 2b, the first and second zine I Z and II Z are concentrical so the arrows f' indicating the upwards flow of the urea melt in the first zone I Z are located left and right of the arrow f" indicating the downwards flow of the urea melt in the second zone II Z.

Figure 3A:
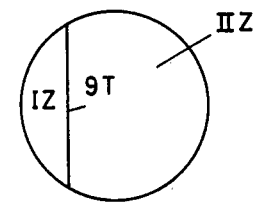
Figure 3B:
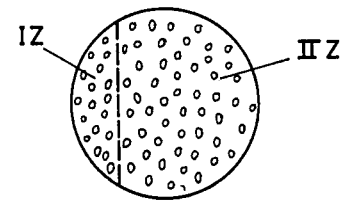

FIGS. 3–3a and 3b show the decomposer treating device embodiment where the two zones I Z and II Z are not concentrical, but placed side-to-side, the first zone I Z is a portion of the left half of the decomposer body CC while the second zone II Z is all the residual portion of the body CC.

For both the described embodiments we have now purposely given a detailed constructive description of the treating device (decomposer) according to the invention, in fact the decomposer main parts can be built with conventional pieces (tube bundle tube sheet, feed manifold, etc.) of the type largely used in reactors, strippers, decomposers and the alike, conventionally used in urea production and in chemical industries in general. The invention concerns therefore, besides the treating process, the new decomposer structure, which may then be formed by the assembling of known pieces.

EXAMPLE I A

The decomposer or stripper used in the conventional technology, according to the reference II, is fed with the urea melt having the following averaged characteristics.

| Composition: | | |
|---|---|---|
| $NH_3$ | 45.33 kg. | *operating conditions of the synthesis reactor $NH_3$ = 2.8 urea reactor yield 60% |
| $CO_2$ | 29.33 kg. | |
| Urea | 60 kg. (1 k mole) | |
| $H_2O$ | 36 kg | |
| Total | 170.66 kg. | |

According to the article by Kaasenbrood in Fertilizers Society Proceeding No. 166, December 77 the decomposer according to reference II is sized with the following criterion: Two tubes each K mole of treated urea are used, each tube having an internal diameter Di=25 mm and length L=6 m. It is important to mention that in order to improve the yield in the synthesis reactor that produces the urea melt fed to the above-mentioned stripper, the reactor should be operated with a molar ratio $NH_3:CO_2$ higher than 2.8 and equal, for example, to 4. But in this case with $NH_3/CO_2$ ratio=4 the vapor flow in the decomposer would have an increase and require the use of tubes having a diameter greater than 25 mm (approximately Di=30 mm) and a shorter length, approximately L=4.3 m (to avoid flooding and to reduce the total surface of the decomposer proportionally to the increased yield 60/70).

According to reference II for a 1000 MT/d (metric Tons/Day) urea plant, that is 41,666 kg/h=694.4 K moles/h urea, a decomposer with 694.4×2=1388 tubes should be required-with Di=25 mm ($NH_3/CO_2$=2.8) or Di=30 mm ($NH_3/CO_2$=4). The decomposer weight increase in this last case (Di=30 mm) would be 25 tons (total estimated weight 100 t), with equipment cost increase of 25,000 kg×7,500 lit/kg=187.5 million Lire (ca. US $225,000).

EXAMPLE 1B

When the two step process according to the present invention is used, it is possible to operate with a decomposer of the type of FIGS. 2 or 3 whereby the first decomposition zone I Z is fed with a urea melt showing the following characteristics:

| Composition | |
|---|---|
| I Zone | *Operating conditions of the synthesis reactor molar ratio of |

-continued

| Composition | | | |
|---|---|---|---|
| NH₃ | 63.13 kg. | NH₃/CO₂ = | 4 |
| CO₂ | 18.85 kg. | Urea reactor yield | 70% |
| Urea | 60 kg. (1k mole) | Pressure: 160 bar | |
| H₂O | 33.42 kg. | Temperature: 190° | |
| Total | 175.40 kg. | | |

With a urea flow of 1000 kg. in each tube (having, for example, a diameter $D_i=20$ mm and a length $L=6$ m) the tube number (N'T) of the treating device decomposer TD first zone I Z for a 1000 MT/d plant (694.4 urea K moles/h) is $$N'T = \frac{175.5 \times 694.4}{1'000} = 122 \text{ tubes.}$$

The first zone I Z is heated with steam at a temperature of 200° C. The urea solution UM residence time in this I Z is of 3 seconds. The compositions CI of the urea melt UM' that, after the first zone treatment, enters ST of the second zone II Z of the decomposer is:

| | | |
|---|---|---|
| NH₃ | 39 kg. | |
| CO₂ | 15.5 kg. | |
| Urea | 60 kg. (1 k mole) | |
| H₂O | 29.3 kg. | |
| Total | 143.8 kg. | |

Feeding into the treating device TD (decomposer) 22 kg. of fresh stripping CO₂ through nozzle 6 (about ½ k mole CO₂ each k mole urea) upwards countercurrently with the urea melt flowing downwards into the second zone tubes (heated at 200° C.) a urea melt with the following composition expressed in weight percent is collected in the lower bottom piece and discharged from nozzle 5:

NH₃=4 kg. (5 wt.%), CO₂=1.6 kg. (2 wt.%), urea=60 kg. (75 wt.%) H₂O=14.4 kg. (18 wt.%). The residence time of the melt in the second zone was 15 seconds.

In the decomposer upper head piece through nozzle 4 a vapor flow with the following composition is discharged:

NH₃—59.13 kg.; CO₂ 17.25+22 kg.; H₂O=19 kg.
With a design flow for the second zone of 100 kg. each tube having inside diameter $D_i=20$ mm and length $L=6$ m the number of tubes (N'T) is:

$$N'' = \frac{143.8 \times 694.4}{100} = 999 \text{ tubes.}$$

The total tubes number for first and second zone is N'T+N"T 122+999=1121.

The decomposer weight reduction with reference to Example IA (1388 tubes Di=25 mm) is 27,000 kg. with a saving of 27,000 kg.×7500 lit/kg.=202.5 million lire (about 243,000 US $). This saving is calculated without taking into account the reactor yield difference (70% in the example according to the invention and 60% according to the conventional technology in Example 1A); if this improvement is also considered another saving of 187.5 million lire should be added to the 202.5 million lire. The above-mentioned results are also true when no stripping agent is used (CO₂=0). The urea melt discharged from nozzle 5 will be in the absence of fresh CO₂:

NH₃=8 kg. (9.4 wt.%) CO₂=2.6 kg. (3 wt.%); urea 60 kg. (70.1 wt.%) H₂O 15 kg. (17.5 wt.%).

EXAMPLES 2A and 2B (2A) According to the Italian Pat. No. 770,241 (reference IV) the urea melt composition after the two stages decomposer is:

| | | |
|---|---|---|
| NH₃ | | 36.7 wt. % |
| CO₂ | | — |
| Urea | | 46 |
| H₂O | | 17.3 |
| | Total | 100 wt. % |

(2B) According to the Auslegeschrift No. 1,468,628 (I) the urea melt (UM') composition issuing from the decomposer is:

| | | |
|---|---|---|
| NH₃ | | 47.79 wt. % |
| CO₂ | | 0.95 wt. % |
| Urea | | 39.41 wt. % |
| H₂O | | 11.85 |
| | Total 100 | wt. % |

EXAMPLE 2C

With the use of the treatment process and of a decomposer according to the present invention (operating at the reactor pressure of 160 bar and at 200° C. temperature: isobaric loop), the urea melt composition (expressed in wt.%) at the outlet of the decomposer second zone (II Z heated at 200° C.) is: (a) using a CO₂ stripping of 22 kg. (b) using no CO₂ stripping

| (a) | | (b) | |
|---|---|---|---|
| NH₃ | 5 wt. % | NH₃ | 9.4 wt. % |
| CO₂ | 2 wt. % | CO₂ | 3 wt. % |
| Urea | 75 wt. % | Urea | 70.1 wt. % |
| H₂O | 18 wt. % | H₂O | 17.5 wt. % |
| Total | 100 | | |

The residence time in the first and second zones were of 11 seconds and 15 seconds, respectively.

By comparing the figures according to Example 2C (use of the invention) with those of the comparison Examples 2A and 2B (use of the conventional systems), the advantages of the invention are clearly apparent and consist substantially in that the expensive devices required, for example, in reference I downstream the stripper to purify and recycle the high excess residual ammonia in the urea melt are avoided.

The important advantages of the process and treating device according to the present invention can be summarized as follows:

(1) Because in the first process step in the relative decomposer first zone I Z, the urea solution and the distillaed gas are flowing upwards cocurrently, the first step space or first zone can be designed (sized) in an optimal manner even in the presence of heavy amounts of gas developed in the solution distillation, particularly when the urea solution UM comes from a synthesis reactor containing a large excess of free NH₃: accordingly all problems of flooding are avoided. The first concurrent treatment step will not require external passivation air injection since the heating surface is passivated by the air already contained in the urea solution coming from the reactor. If a countercurrent is used as in conventional processes the air would be "stripped off" before reaching the lower and hottest part of the equipment.

(2) Sizing of the second step space, particularly of the decomposer second zone (II Z) is no more critical, not even when a stripping agent $CO_2$ is used countercurrently with the urea melt because a heavy amount of vapors has been separated in the first zone (I Z). The reduced second step surface will minimize the quantity of passivating air required to prevent corrosion.

(3) First and second zone sizing can be optimized for best process performances.

(4) Urea melts containing high quantities of free ammonia and coming from high yield reactors (high $NH_3/CO_2$ molar ratios) can be treated in the process, respectively, the decomposer according to the invention. In such cases, by operating the decomposer at pressures which can be below those of the synthesis reactors, the invention offers the ideal means for the best treatment of the urea melts very rich in free ammonia because its decomposer is just designed to eliminate the maximum of $NH_3$ in its first step while the largest quantity of carbammate is decomposed more easily only in the second step.

(5) The final urea melts (UM'') which have undergone the treatment of the invention and come out from the relative decomposers of FIGS. 2 and 3 show a very low residual content of carbamate and free $NH_3$ whereby they require no important further treatment with consequent important savings in plant treatment down-stream from the decomposer.

(6) Lower quantities of stripping agent ($CO_2$) can be used, compared with those necessary in the prior art.

(7) The two step treatment and the relative decomposer can be operated at reactor pressure.

With reference to the above items and in particular to the advantages of item (4), the following considerations are usefully added: it is not possible to use the carbammate decomposer according to reference (II) of the prior art for treating a urea melt having a high $NH_3$ content, due to the very high vapor ($NH_3$) flow in the stripper operated with a countercurrent of stripping $CO_2$ (plus $NH_3$ vapor, etc.) whereby a very large decomposer tube cross section would be required and as a consequence a very high equipment cost would be involved.

Furthermore, the high $NH_3$ vapor content would reduce the carbammate decomposition efficiency, the $NH_3$ excess having a diluting effect on the $CO_2$ content of the vapor phase; in this case $CO_2$ vapor concentration should be maximum, $CO_2$ being the stripping agent. According to reference II a low $NH_3/CO_2$ ratio must be kept in the synthesis reactor with low urea yield (Max. $NH_3/CO_2=2.85$ at 140 bar); on the contrary the process and the decomposer according to the present invention can be operated economically in combination with high $NH_3/CO_2$ ratio reactors and high urea yields are achieved without problems in the carbammate decomposition step.

We wish finally to point out that a technician skilled in the art, starting from the available teaching in the literature, (reference III and II) would have conceived the two-step treatment so that the bulk of carbammate is decomposed in step I, while step II is used only for the distillation of residual ammonia and carbammate (the functions of the two steps are inverted in respect to the present invention).

This solution would have been very impractical, requiring two countercurrent steps in series (when operating at high pressure a high carbammate decomposition can only be achieved using the known countercurrent "stripping technique"). A two-step countercurrent treatment implies the use of costly falling film apparatus, and the first step treatment would present the flooding problems described, especially when ammonia rich urea solutions have to be treated. A high quantity of passivating air would also be required with the disadvantages already described. If the bulk of carbammate is decomposed in the first step the free ammonia still contained in the second step feeding solution would react with the $CO_2$ stripping agent to form carbammate again. This parasite reaction, that could be avoided operating at high temperatures with corrosion danger, would cause an increase in the stripping agent flow. Obviously when the treatment of the invention is carried out at pressures lower than the synthesis pressure, the first step can be carried out without heat supply but only by flashing separation.

The embodiments of the invention in which an exclusive property or privilege is claimed are defined as follows:

1. A process for the treatment of urea solutions obtained from high yield synthesis reactors wherein ammonia in excess over the stoichiometric ratio and carbon dioxide are reacted under pressure and at high temperature, and containing in addition to urea, free ammonia, water, unreacted ammonium carbamate, and other by-products, comprising:

(a) a first distillation step in which a substantial amount of free ammonia is distilled from the urea solution and the unreacted ammonium carbamate only partially decomposed, comprising heating said solution at a temperature of between 190°–230° C. at a pressure of at least 100 bars for a period less than 50 seconds resulting in the upward flow of said urea solution concurrently with gaseous material, and (b) a second decomposition by stripping and distillation step in which a substantial amount of the ammonium carbamate is decomposed and the remaining $NH_3$ is distilled from the urea solution, comprising heating said solution at a temperature of 190°–230° C. at a pressure of at least 100 bars for a period of at most 60 seconds while the urea solution is flowing downwards and in countercurrent contact with the gases produced therefrom.

2. A process as claimed in claim 1, wherein the period of step (a) is from 3 to 12 seconds.

3. A process as claimed in claim 1, wherein the period of step (b) is from 10 to 20 seconds.

4. A process as claimed in claim 1, wherein a countercurrent of $CO_2$ is introduced in step (b).

* * * * *

UNITED STATES PATENT AND TRADEMARK OFFICE
CERTIFICATE OF CORRECTION

PATENT NO. : 4,269,997
DATED : May 26, 1981
INVENTOR(S) : Primo Pastormerlo

It is certified that error appears in the above-identified patent and that said Letters Patent are hereby corrected as shown below:

On the title page,

[30] Foreign Priority Data
"Italy 26020 A/78" should be
--Italy 26010 A/78--

Signed and Sealed this

Eighteenth Day of August 1981

[SEAL]

Attest:

GERALD J. MOSSINGHOFF

Attesting Officer

Commissioner of Patents and Trademarks